US011946835B2

(12) United States Patent
Chrin

(10) Patent No.: US 11,946,835 B2
(45) Date of Patent: *Apr. 2, 2024

(54) GAS SAMPLING AND MANAGEMENT SYSTEM

(71) Applicant: Chrintec, LLC, Easton, PA (US)

(72) Inventor: Gregory R. Chrin, Easton, PA (US)

(73) Assignee: Chrintec, LLC, Easton, PA (US)

(*) Notice: Subject to any disclaimer, the term of this patent is extended or adjusted under 35 U.S.C. 154(b) by 73 days.

This patent is subject to a terminal disclaimer.

(21) Appl. No.: 17/751,289

(22) Filed: May 23, 2022

(65) Prior Publication Data

US 2022/0373435 A1 Nov. 24, 2022

Related U.S. Application Data

(63) Continuation of application No. 16/708,835, filed on Dec. 10, 2019, now Pat. No. 11,340,146, which is a
(Continued)

(51) Int. Cl.
*G01N 1/22* (2006.01)
*G01N 33/00* (2006.01)
*G05D 7/06* (2006.01)

(52) U.S. Cl.
CPC ......... *G01N 1/2247* (2013.01); *G01N 1/2273* (2013.01); *G01N 33/0036* (2013.01);
(Continued)

(58) Field of Classification Search
CPC ............... G01N 1/2247; G01N 1/2273; G01N 33/0036; G01N 33/0062; G01N 33/0073
(Continued)

(56) References Cited

U.S. PATENT DOCUMENTS 3,490,288 A 1/1970 Whitman
3,685,345 A 8/1972 Wise
(Continued)

FOREIGN PATENT DOCUMENTS

DE 19610402 2/1997
WO 2014/107370 7/2014

OTHER PUBLICATIONS

Fay, et al.; Remote Real-Time Monitoring of Subsurface Landfill Gas Migration; Sensors 2011, 11, 6603-6628; www.mdpi.com/journal/sensors; 26 pages.
(Continued)

*Primary Examiner* — Alexander A Mercado
*Assistant Examiner* — Rodney T Frank
(74) *Attorney, Agent, or Firm* — Morgan, Lewis & Bockius LLP

(57) ABSTRACT

A gas monitoring and control system including a gas sampling chamber, sampling inlet and outlet valves, a pump and a controller. Sensors are disposed within the interior chamber that sense characteristics of a gas from a gas source and generate representative signals. The sampling inlet and outlet valves i) allow the gas into the gas sampling chamber while operating in a gas sampling state, and ii) allow ambient air into the gas sampling chamber while operating in a purge state. The pump i) causes the gas to flow through the gas sampling chamber while operating in the gas sampling state or ii) causes ambient air to flow through the gas sampling chamber while operating in the purge state. The controller causes the sampling inlet and outlet valves, and the pump to alternate operating in the gas sampling or purge state to selectively expose the sensors to the gas.

13 Claims, 10 Drawing Sheets

Related U.S. Application Data continuation of application No. 15/374,587, filed on Dec. 9, 2016, now Pat. No. 10,533,930, which is a continuation of application No. 15/046,009, filed on Feb. 17, 2016, now Pat. No. 9,677,976.

(60) Provisional application No. 62/117,330, filed on Feb. 17, 2015.

(52) U.S. Cl.
CPC ..... *G01N 33/0062* (2013.01); *G01N 33/0073* (2013.01); *G05D 7/0635* (2013.01); *G01N 1/2294* (2013.01); *Y02W 30/30* (2015.05)

(58) Field of Classification Search
USPC ....................................................... 73/31.03
See application file for complete search history.

(56) References Cited

U.S. PATENT DOCUMENTS

| | | | |
|---|---|---|---|
| 4,026,355 A | 5/1977 | Johnson et al. | |
| 4,444,041 A | 4/1984 | Zison | |
| 4,890,672 A | 1/1990 | Hall | |
| 5,063,519 A | 11/1991 | Zison | |
| 5,355,739 A | 10/1994 | Cooper et al. | |
| 5,611,844 A | 3/1997 | Troost et al. | |
| 5,650,560 A | 7/1997 | Troost | |
| 5,695,641 A | 12/1997 | Cosulich et al. | |
| 5,744,730 A | 4/1998 | Ballard et al. | |
| 5,786,527 A | 7/1998 | Tarte | |
| 5,888,022 A | 3/1999 | Green | |
| 6,591,695 B1 | 7/2003 | Brookshire et al. | |
| 6,661,233 B2 | 12/2003 | Yang et al. | |
| 6,670,887 B2 | 12/2003 | Dungan | |
| 6,994,491 B2 | 2/2006 | Kittle | |
| 6,999,883 B1 | 2/2006 | Brady et al. | |
| 7,281,439 B2 | 10/2007 | Schmitt et al. | |
| 7,526,944 B2 | 5/2009 | Sabata et al. | |
| 7,972,082 B2 | 7/2011 | Augenstein et al. | |
| 8,021,612 B2 | 9/2011 | Tooley | |
| 8,163,242 B2 | 4/2012 | Elkins | |
| 8,168,121 B2 | 5/2012 | Elkins | |
| 8,311,723 B2 | 11/2012 | McAlister | |
| 8,404,184 B2 | 3/2013 | Tooley | |
| 8,678,348 B1 | 3/2014 | Cassel et al. | |
| 9,062,536 B2 | 6/2015 | Fischer et al. | |
| 9,677,976 B2 * | 6/2017 | Chrin, II | G01N 33/0062 |
| 10,533,930 B2 * | 1/2020 | Chrin | G01N 33/0062 |
| 2003/0136174 A1 | 7/2003 | Edwards et al. | |
| 2005/0163571 A1 | 7/2005 | Kittle | |
| 2007/0243023 A1 | 10/2007 | Augenstein et al. | |
| 2007/0266800 A1 | 11/2007 | Risk | |
| 2008/0028826 A1 | 2/2008 | Schmitt et al. | |
| 2009/0301234 A1 | 12/2009 | Risk | |
| 2010/0005812 A1 | 1/2010 | Watts et al. | |
| 2010/0192683 A1 | 8/2010 | Elkins | |
| 2011/0231099 A1 | 9/2011 | Elkins | |
| 2012/0011104 A1 | 1/2012 | Tooley | |
| 2012/0035850 A1 | 2/2012 | Risk | |
| 2012/0191349 A1 | 7/2012 | Lenz et al. | |
| 2012/0206715 A1 | 8/2012 | Laub | |
| 2012/0297868 A1 | 11/2012 | Elkins | |
| 2013/0236840 A1 | 9/2013 | Maslov et al. | |

OTHER PUBLICATIONS

International Patent Application No. PCT/US2016/018265; Notification of Transmittal of the International Search Report and the Written Opinion of the International Searching Authority, or the declaration, dated May 6, 2016, 9 pages.
Gregory Chrin, "Linc", Brochure, first available on Apr. 7, 2015, 1 page.
"Loci Controls", www.locicontrols.com, retrieved Feb. 20, 2015, 2 pages.
International Patent Application No. PCT/US2016/018265; Notification Concerning Transmittal of International Preliminary Report on Patentability (Chapter 1 of the Patent Cooperation Treaty), dated Aug. 31, 2017, 9 pages.
Landfill Gas Operation and Maintenance Manual of Practice, National Renewable Energy Laboratory (NREL), Mar. 1997. www.nrel.gov/docs/legosti/fy97/23070.pdf.
"Field Procedures Handbook for the Operation of Landfill Biogas Systems." Https://Www.iswa.org, International Solid Waste Association Working Group for Sanitary Landfills, 2005, www.iswa.org/index.php?eID=tx_bee4memeberships_download&fileUid=99.

* cited by examiner

GAS SAMPLING AND MANAGEMENT SYSTEM

CROSS-REFERENCE TO RELATED APPLICATIONS

This application is a continuation of U.S. patent application Ser. No. 16/708,835, filed Dec. 10, 2019, which is a continuation of U.S. patent application Ser. No. 15/374,587, filed Dec. 9, 2016, which is a continuation of U.S. patent application Ser. No. 15/046,009, filed Feb. 17, 2016, now U.S. Pat. No. 9,677,976 which issued Jun. 13, 2017, which claims the benefit of U.S. Provisional Patent Application No. 62/117,330 filed Feb. 17, 2015 entitled "GAS EXTRACTION AND TRANSPORT MANAGEMENT SYSTEM", each of which is incorporated by reference herein in its entirety.

BACKGROUND

The present invention generally relates to gas monitoring system and, more particularly, to systems and methods for gas monitoring.

Millions of ions of garbage are deposited into landfills each year. As the garbage decomposes, it produces a number of harmful gases. Landfill gas is composed of approximately, equal parts (fifty percent (50%)) of methane and carbon dioxide, both of which are greenhouse gases. Methane has a malicious environmental impact nearly twenty (20) times greater than that of carbon dioxide over a period of 100 (one hundred) years, According to the Environmental Protection Agency, landfills contributed approximately eighteen percent (18%) to overall methane emissions in the U.S. in 2012.

To minimize the harmful effects of the landfill gas, landfills extract the gas and then burn or neutralize it before the gas can escape into the atmosphere. Landfills utilize hundreds of gas extraction wells to perform this function. In operation, the well system creates a negative pressure in the decomposing trash causing the gas to evacuate from the landfill. The gas from multiple wells is then collected using a main gas line and transported to a flare where it will be burned off or to an energy facility where it will be used to generate a form of renewable energy.

In some situations, such as when oxygen from ambient air mixes into the landfill gas at the landfill area, the landfill gas's energy effectiveness is diminished. In these situations, it is more effective to regulate the amount of gas evacuating from the landfill area until the landfill gas composition becomes more favorable. To regulate gas evacuation, gas wells are fitted with valves. The valves can be positioned in varying configurations to regulate an amount of landfill gas evacuating to the main gas line. Due to frequent variations in the composition of the landfill gas, the gas wells are tuned fastidiously and frequently to ensure proper well field operation. Currently, a technician physically travels to each gas well and measures the landfill gas. The technician then regulates the amount of gas evacuating from the gas well based on the landfill gas measurements. This process is costly and time consuming, because a technician must travel to each of the hundreds of wells. Also, because the tuning occurs infrequently, gas extraction is less effective.

Additionally, in some situations, gas wells may unexpectedly break or crack, allowing harmful landfill gas to leak into the environment. Currently, a technician can only detect the gas leak when the technician is in proximity to the gas well. Because the technician may visit the gas well infrequently, a substantial amount of harmful landfill gas may leak into the environment before detection occurs, causing environmental concerns and producing unpleasant odors for local residents.

SUMMARY

In some embodiments, there is a gas monitoring and control system including a gas sampling chamber having a chamber inlet, a chamber outlet and an interior chamber; one or more sensors disposed within the interior chamber, the sensors being operable to sense one or more characteristics of a gas from a gas source and generate one or more sensor signals representative of the one or more characteristics of the gas; a sampling inlet valve in operable communication with an outlet of the gas source and the chamber inlet; a sampling outlet valve in operable communication with the chamber outlet and an inlet of the gas source, the sampling inlet valve and the sampling outlet valve are operable to i) allow the gas from the gas source to enter the gas sampling chamber while operating in a gas sampling state, and ii) allow ambient air to enter the gas sampling chamber while operating in a purge state, a pump in operable communication with the sampling inlet valve and the sampling outlet valve, the pump operable to i) cause the gas to flow through the gas sampling chamber while operating in the gas sampling state and ii) cause ambient air to flow through the gas sampling chamber while operating in the purge state; and/or a controller in operable communication with the one or more sensors, the sampling inlet valve, the sampling outlet valve and the pump, the controller operable to cause the sampling inlet valve, the sampling outlet valve and the pump to alternate operating in the gas sampling state during a sampling time period and the purge state during a purge time period to selectively expose the one or more sensors to the gas.

In some embodiments, the sampling time period is less than 2 minutes.

In some embodiments, a time interval between subsequent sampling time periods is greater than 1 hour.

In some embodiments, the sampling inlet valve and the sampling outlet valve are operable to facilitate creating a static pressure in the gas sampling chamber while operating in a vacuum pressure state; and wherein the controller is operable to cause the sampling inlet valve and the sampling outlet valve to each operate in the vacuum pressure state during a vacuum pressure time period.

In some embodiments, the sampling inlet valve and the sampling outlet valve are operable to isolate the gas sampling chamber from the gas while operating in an isolation state; and wherein the controller is operable to cause the sampling inlet valve and the sampling outlet valve to each operate in the isolation state during an isolation time period.

In some embodiments, the purge time period is less than 2 minutes.

In some embodiments, the controller is operable to cause the sampling inlet valve, the sampling outlet valve and the pump to operate in the gas sampling state in response to receiving a sampling command from an external computing device to sample the gas.

In some embodiments, the gas monitoring and control system includes a valve actuator in operable communication with a gas source valve in the gas source; and wherein the controller is in operable communication with the valve actuator and operable to cause the valve actuator to transition the gas source valve towards an open position or a closed position when the one or more sensor signals meets valve actuation criteria to regulate the flow of landfill gas in the wellhead.

In some embodiments, the one or more sensor signals includes a sensor signal representative of oxygen concentration of the gas.

In some embodiments, the one or more sensor signals meets valve actuation criteria when the one or more sensor signals exceeds a concentration threshold; and in response, the controller causes the valve actuator motor to transition the gas source valve towards the closed position.

In some embodiments, the one or more sensor signals meets valve actuation criteria when the one or more sensor signals falls below a concentration threshold; and in response, the controller causes the valve actuator motor to transition the gas source valve towards the open position.

In some embodiments, the one or more sensor signals meets valve actuation criteria when a positive rate of change of the one or more sensor signals exceeds a concentration change rate threshold; and in response, the controller causes the valve actuator motor to transition the gas source valve towards the closed position.

In some embodiments, the one or more sensor signals meets valve actuation criteria when a negative rate of change of the one or more sensor signals exceeds a concentration change rate threshold; and in response, the controller causes the valve actuator motor to transition the gas source valve towards an open position.

In some embodiments, the controller is operable to cause the valve actuator motor to transition the gas source valve towards the open position or the closed position when a second set of one or more sensor signals sampled at a second gas source meets valve actuation criteria.

In some embodiments, the second set of one or more sensor signals meets valve actuation criteria when the second set of one or more sensor signals is less than the one or more sensor signals; and in response, the controller is operable to cause the valve actuator motor to transition the gas source valve towards the open position.

In some embodiments, the second set of one or more sensor signals meets valve actuation criteria when the second set of one or more sensor signals is greater than the one or more sensor signals; and in response, the controller is operable to cause the valve actuator motor to transition the gas source valve towards the closed position.

BRIEF DESCRIPTION OF THE SEVERAL VIEWS OF THE DRAWINGS

The foregoing summary, as well as the following detailed description of embodiments of the invention, will be better understood when read in conjunction with the appended drawings of an exemplary embodiment. It should be understood, however, that the invention is not limited to the precise arrangements and instrumentalities shown.

In the drawings.

DETAILED DESCRIPTION

Figure 1:
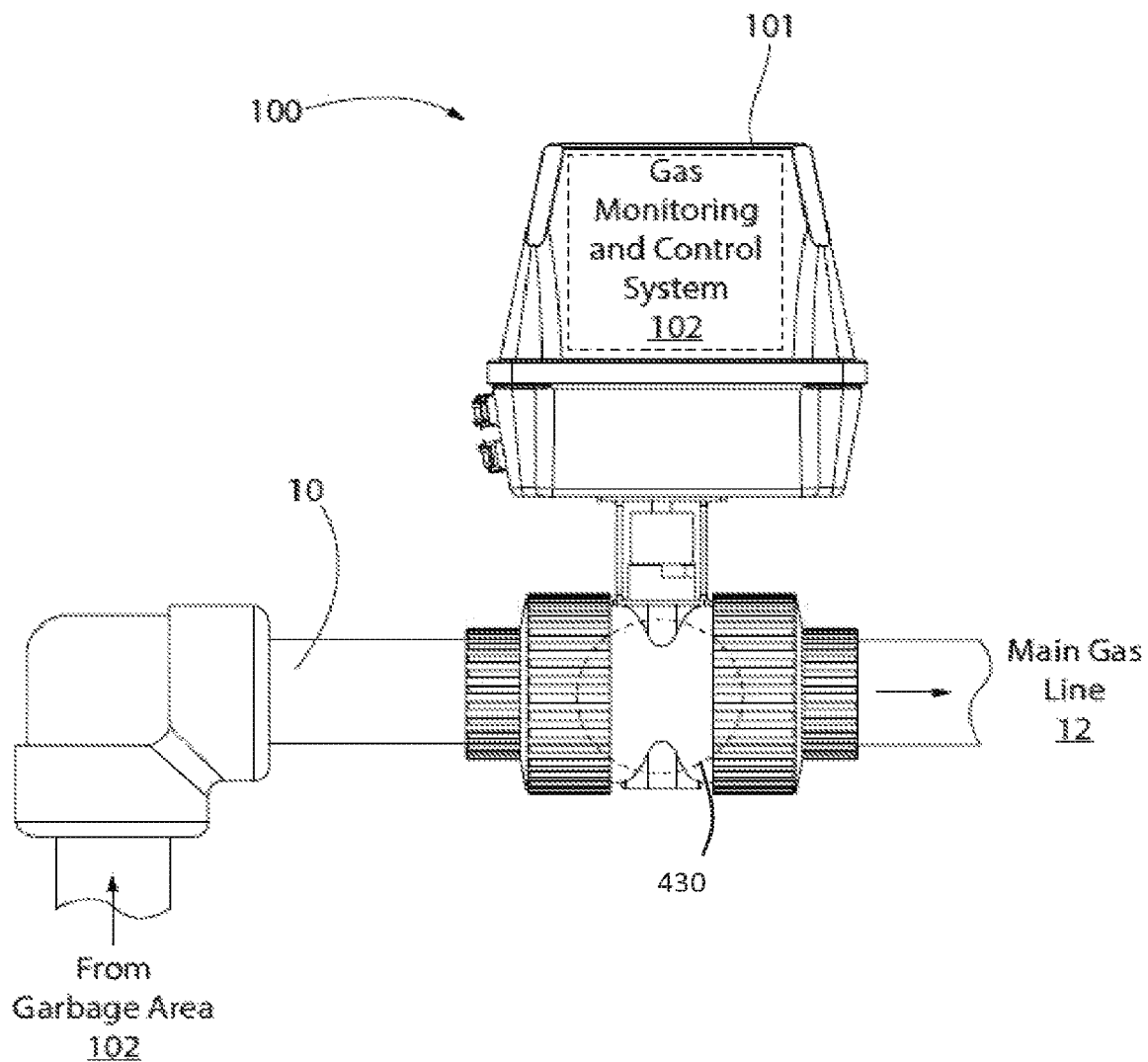
FIG. 1 is a side view of a gas wellhead and a system configured to monitor gas from a wellhead and control gas traveling from a landfill area to a main gas line, according to at least one embodiment of the invention.

Embodiments of the invention allow for efficient monitoring and tuning of a wellhead. By providing users with real-time, instantaneous monitoring and control capabilities, embodiments of the invention can detect gas leaks quickly and efficiently, thereby significantly minimize the amount of gas lost by extraction/transport facilities. As a result, embodiments of the invention provide economic and industrial benefits by optimizing production of renewable energy and minimizing environmental risk and enhancing safety for those who maintain, monitor, assess and check the wellheads.

Referring to the drawings in detail, wherein like reference numerals indicate like elements throughout, there is shown in FIGS. 1-6, a system monitoring and controlling gas evacuation, generally designated, in accordance with an exemplary embodiment of the present invention.

FIG. 1 is a side view of a gas wellhead 10 and a system 100 configured to monitor gas from the wellhead 10 and control gas travelling from a landfill area to a main gas line, according to at least one embodiment of the invention. In FIG. 1, the wellhead 10 is connected to a landfill area 11 containing landfill waste. Over time, the landfill waste produces landfill gas. This landfill gas travels from the landfill area 11, through the wellhead 10, to the main gas line 12. Then, the gas may be transported to a flare for incineration or an energy facility for generating renewable energy.

In some embodiments, the system 100 includes a gas monitoring and control system 102 (illustrated, for example, in FIG. 3A) disposed in a housing 101 of system 100. The gas monitoring and control system 102 is couplable to the wellhead 10. The gas monitoring and control system 102 is configured to receive the landfill gas from the wellhead 10, monitor the characteristics of the landfill gas and perform further actions based on the monitored characteristics. For example, in some embodiments, the gas monitoring and control system 102 regulates the amount of landfill gas evacuating from the landfill area 11. Examples for regulating landfill gas evacuation, such as repositioning a wellhead valve 430 (e.g., a ball valve as illustrated in FIG. 1) of wellhead 10 to open or close an aperture in the wellhead 10, are described in more detail below. Alternatively, in some embodiments, the gas monitoring and control system 102 communicates landfill gas data to an external computing device (e.g., a central control system), external to system 100, to alert a technician to problems with the wellhead 10 or main gas line 12. In some embodiments, the gas monitoring and control system 102 receives commands from the external computing device causing the gas monitoring and control system 102 to regulate the amount of landfill gas evacuating from the landfill area 11, As a result of continuous monitoring of the wellhead 10, problems with the landfill gas or wellhead 10 can be detected quickly, allowing for quick regulation of landfill gas transmitted to the main gas line 12 without the need for a technician to manually inspect the wellhead 10.

Gas Monitoring

Figure 2:
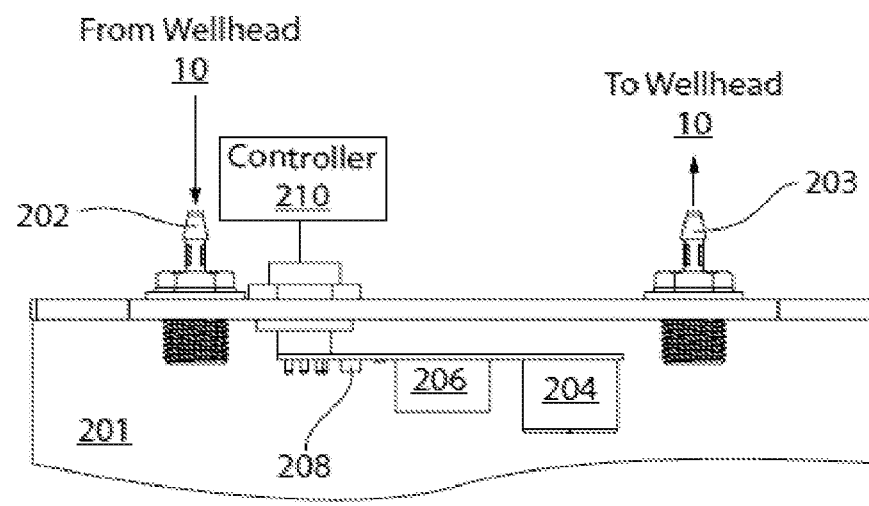
FIG. 2 is a schematic diagram illustrating exemplary components of the gas monitoring and control system, according to at least one embodiment of the invention.

FIG. 2 is a schematic diagram illustrating exemplary components of the gas monitoring and control system 102, according to at least one embodiment of the invention.

In some embodiments, the gas monitoring and control system 102 includes a gas sampling chamber 201. Gas sampling chamber 201 may be configured as an internal chamber located within the wellhead 10. Gas sampling chamber 201 may be configured as a by-pass chamber within a wellhead 10. Gas sampling chamber 201 may be configured to isolate electrical components, such as pumps, controllers and power sources (described in more detail throughout) from the landfill gas.

The gas sampling chamber 201 includes an inlet port 202 configured to receive gas from a source such as the wellhead 10 and an outlet port 203 configured to transport landfill gas to an outlet such as back to the wellhead 10. The gas sampling chamber 201 may be of a fixed volume and may be configured to house one or more sensors (e.g., sensors 204, 206, 208) to measure characteristics of the landfill gas in the wellhead 10. In some embodiments, the gas sampling chamber 201 encloses the one or more sensors in an airtight enclosure to improve sensor measurement accuracy. The sensors may include one or more of an oxygen sensor, a methane sensor, a carbon dioxide sensor, a temperature sensor, pressure sensor, a humidity sensor and a flow rate sensor.

In some embodiments, one of the sensors that may be positioned in the gas sampling chamber 201 is an oxygen sensor 204. The oxygen sensor 204 is an electronic device that measures the concentration of oxygen in the landfill gas. In some embodiments, the oxygen sensor 204 is an optical oxygen sensor. In some embodiments, the oxygen sensor 204 is the LuminOx manufactured by SST Sensing Ltd.

In some embodiments, the gas monitoring and control system 402 includes a methane sensor that may be positioned in the gas sampling chamber 201. The methane sensor is an electronic device that measures the concentration of methane in the landfill gas. In some embodiments, one of the sensors in the gas monitoring and control system 102 is a carbon dioxide sensor that may be positioned in the gas sampling chamber 201. The carbon dioxide sensor is an electronic device that measures the concentration of carbon dioxide in the landfill gas. In some embodiments, and as shown in FIG. 2, one of the sensors in the gas monitoring and control system 102 is a dual methane/$CO_2$ sensor 206 positioned in the gas sampling chamber 201. In some embodiments, the dual methane/$CO_2$ sensor 206 is the SIL1 manufactured by Dynament.

In some embodiments, one or more sensors positioned in the gas sampling chamber 201 may degrade more quickly when exposed to moisture (condensate). To mitigate exposure to condensation that may accumulate at the bottom of gas sampling chamber 201, in some embodiments, the one or more sensors are positioned at a top side (relative to gravity) of the gas sampling chamber 201. In some embodiments, the gas monitoring and control system 102 includes a humidity sensor 208 that may be positioned in the gas sampling chamber 201. The humidity sensor 208 is an electronic device that measures an amount of humidity in the landfill gas. The humidity sensor 208 is used to detect condensate build up in sampling chamber and lines. For example, if a humidity sensor 208 detects humidity in the gas sampling chamber 201 that meets humidity criteria (e.g., measured humidity exceeds a humidity threshold), the controller 210 may cause the gas sampling chamber 201 to be purged with ambient air to reduce humidity and protect the sensors. In some embodiments, the humidity sensor 208 is the HIH-5030 manufactured by HONEYWELL®.

In some embodiments, other examples of sensors include sensors or detectors for determining the presence/amounts of methane, carbon monoxide, chlorine, cyanide, hydrogen, hydrogen sulfide, nitric oxides, nitrogen, sulfur oxides, overall gas composition, differential pressure in the wellhead, wellhead gas and ambient air temperature, applied vacuum pressure of wellhead, and gas flow.

The gas monitoring and control system 102 may also include a controller 210 configured to receive one or more sensor signals from the one or more sensors, process the sensor signals, and transmit the sensor signals to an external computing device. Based on the sensor signals representative of landfill gas composition, the controller 210 may perform further actions, such as generating alerts for technicians or actuating a wellhead valve to open or close the wellhead 10. These actions are described in more detail throughout.

Gas Sampling Routine

Prolonging exposure of the sensors to a harsh surrounding landfill gas environment of can cause the sensors to wear quickly over time. To mitigate sensor wear and degradation, the gas monitoring and control system 102 is configured to selectively expose the sensors to the landfill gas during a pre-selected sampling interval or a sampling interval that is variable based on landfill conditions. Exposure to landfill gas environment on a less frequent or intermitted basis may extend the life of the landfill gas sensors.

Figure 3A:
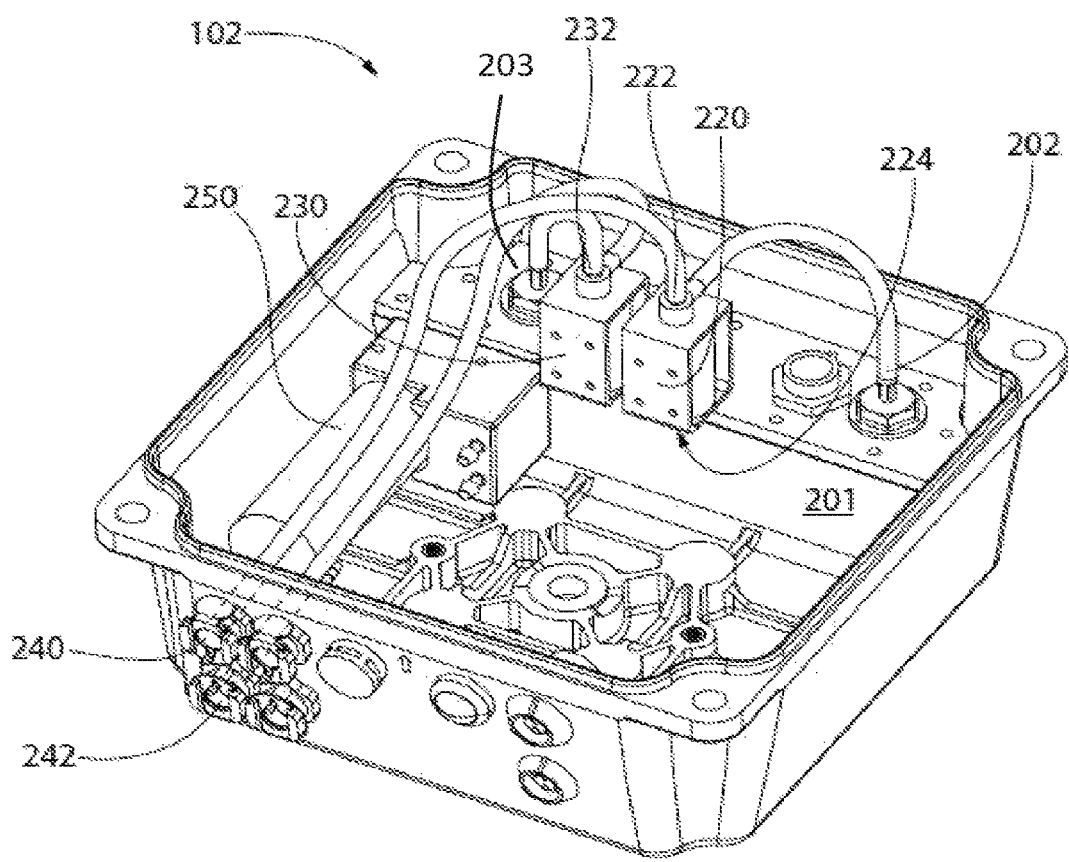
FIG. 3A shows a perspective view of some of the exemplary components of the gas monitoring and control system for sampling landfill gas according to at least one embodiment of the invention.

FIG. 3A shows a perspective view of some of the exemplary components of the gas monitoring and control system 102 for sampling landfill gas according to at least one embodiment of the invention.

In some embodiments, the gas monitoring and control system 102 includes a housing inlet port 240 that allows landfill gas from the wellhead 10 to enter the housing 101. The gas monitoring and control system 102 also includes a housing outlet port 242 that allows landfill gas in the housing to enter the wellhead 10.

In some embodiments, the gas monitoring and control system 102 includes an inlet sampling valve 220 and an outlet sampling valve 230 configured to selectively allow the landfill gas to flow into the gas sampling chamber 201, exposing the sensors to the landfill gas. The inlet sampling valve 220 connects the housing inlet port 240 to the inlet port 202 of gas sampling chamber 201. The outlet sampling valve 230 connects the outlet port 203 (not shown in FIG. 3) of gas sampling chamber 201 to the housing outlet port 242.

The inlet sampling valve 220 includes a landfill gas inlet port 222 that, when open, connects the housing inlet port 240 to the gas sampling chamber 201 to allow landfill gas to enter the gas sampling chamber 201. In some embodiments, the inlet sampling valve 220 is a three-way valve that includes an ambient air inlet port 224. When the ambient air inlet port 224 is open, the inlet sampling valve 220 prevents landfill gas from entering the gas sampling chamber 201. Instead, the inlet sampling valve 220 allows ambient air to enter the gas sampling chamber 201.

The outlet sampling valve 230 includes an inlet port 232 that, when open, connects the outlet port 203 of the gas sampling chamber 201 (not shown) to the housing outlet port 242 and allows landfill gas or ambient air to evacuate into the wellhead 10.

The sampling valves 220, 230 are configured to selectively and temporarily allow landfill gas to enter the gas sampling chamber 201 so that sensors positioned in the gas sampling chamber 201 can measure the composition of the landfill gas while minimizing the amount of time the sensors are exposed to the landfill gas. For example, after exposing the one or more sensors in the gas sampling chamber 201 to landfill gas, the sampling valves are configured to allow ambient air to enter the gas sampling chamber 201 to purge the landfill gas from the gas sampling chamber 201.

In some embodiments, the inlet sampling valve 220 and outlet sampling valve 2:30 each operate in different operating states. When the inlet sampling valve 220 is a three-way valve and is in a first operating state, the inlet sampling valve 220 opens the landfill gas inlet port 222 and connects the housing inlet port 240 to the gas sampling chamber 201, thereby allowing landfill gas to flow into the gas sampling chamber 201. When the inlet sampling valve 220 is in a second operating state, the inlet sampling valve opens the ambient air inlet port 224, thereby allowing ambient air to flow into the gas sampling chamber 201. When the outlet sampling valve 230 is in a first operating state, the inlet port 232 is open, thereby allowing landfill gas or ambient air to evacuate to the gas sampling chamber 201, When the outlet sampling valve is in a second operating state, the inlet port 232 is closed, thereby preventing landfill gas or ambient air to evacuate to the gas sampling chamber 201.

In some embodiments, the controller 210 is connected to the inlet sampling valve 220 and the outlet sampling valve 230. In these embodiments, the controller 210 causes the sampling valves 220, 230 to operate in a selected operating state. For example, in some embodiments, the sampling valves are solenoid valves. In these embodiments, the controller 210 transmits an electrical control signal (e.g., electric current) to cause each of the sampling valves to operate in a selected operating state, either by maintaining a sampling valve in the current operating state or by causing a sampling valve to transition to the operating state. In some embodiments, if the valve receives an electrical control signal from the controller 210 that meets operating state criteria (e.g., electrical current exceeds a selected threshold), the valve operates in a first operating state. In these embodiments, if the valve receives electrical power from the controller 210 that does not meet the operating state criteria, the valve operates in a second operating state.

In some embodiments, the gas monitoring and control system 102 includes a gas sampling pump 250. The gas sampling pump 250 is configured to pump landfill gas or ambient air into and through the gas sampling chamber 201 after the gas sampling pump 250 receives an electrical control signal (e.g., electrical power) from the controller 210. As a result, the gas sampling pump 250, in conjunction with the sampling valves, causes landfill gas to selectively enter the gas sampling chamber 201 and causes selective purging of the landfill gas from the gas sampling chamber 201 based on electrical control signals received from the controller 210.

Using the controller 210, the gas monitoring and control system 102 can operate in, and alternate between, multiple operating phases to measure characteristics of the landfill gas while also limiting the one or more sensors in the gas sampling chamber 201 to landfill gas. Examples of these operating phases include gas sampling phase, vacuum measurement phase, purge phase and sensor isolation phase.

Figure 3B:
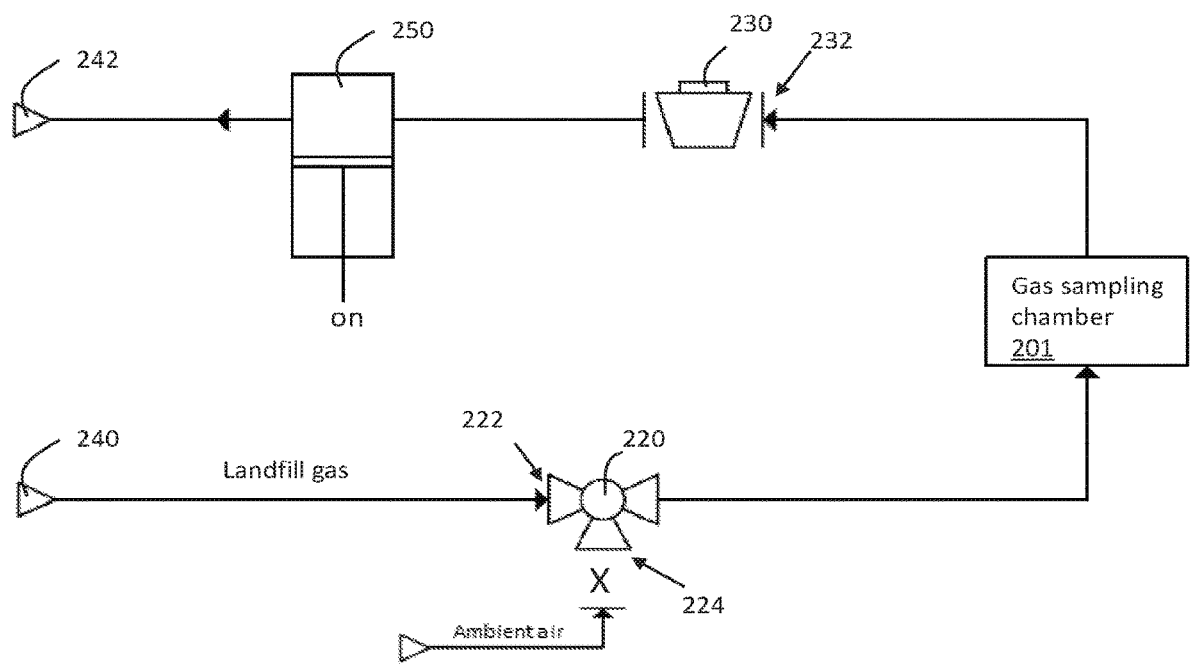
FIG. 3B is a process flow diagram illustrating exemplary components of the gas monitoring and control system of FIG. 3A implementing a gas sampling phase, according to at least one embodiment of the invention.

FIG. 3B is a process flow diagram illustrating exemplary components of the gas monitoring and control system of FIG. 3A implementing a gas sampling phase, according to at least one embodiment of the invention. In the gas sampling phase, the controller 210 causes the inlet sampling valve 220, the outlet sampling valve 230 and the gas sampling pump 250 to operate in a gas sampling state. In these embodiments, the controller 210 causes the landfill gas inlet port 222 of the inlet sampling valve 222 and the inlet port 232 of the outlet sampling valve 230 to open, allowing landfill gas to flow through the gas sampling chamber 201. In some embodiments, the controller 210 also causes the gas sampling pump 250 to pump landfill gas (i.e., turn on) into and through the gas sampling chamber 201. In some alternative embodiments, negative pressure created in the wellhead 10 may cause landfill gas to flow into and through the gas sampling chamber 201, without the use of gas sampling pump 250. During the gas sampling phase, the one or more sensors positioned in the gas sampling chamber 201 measure the composition of the landfill gas. The sensor output signals are subsequently transmitted to the controller 210 for further processing.

Figure 3C:
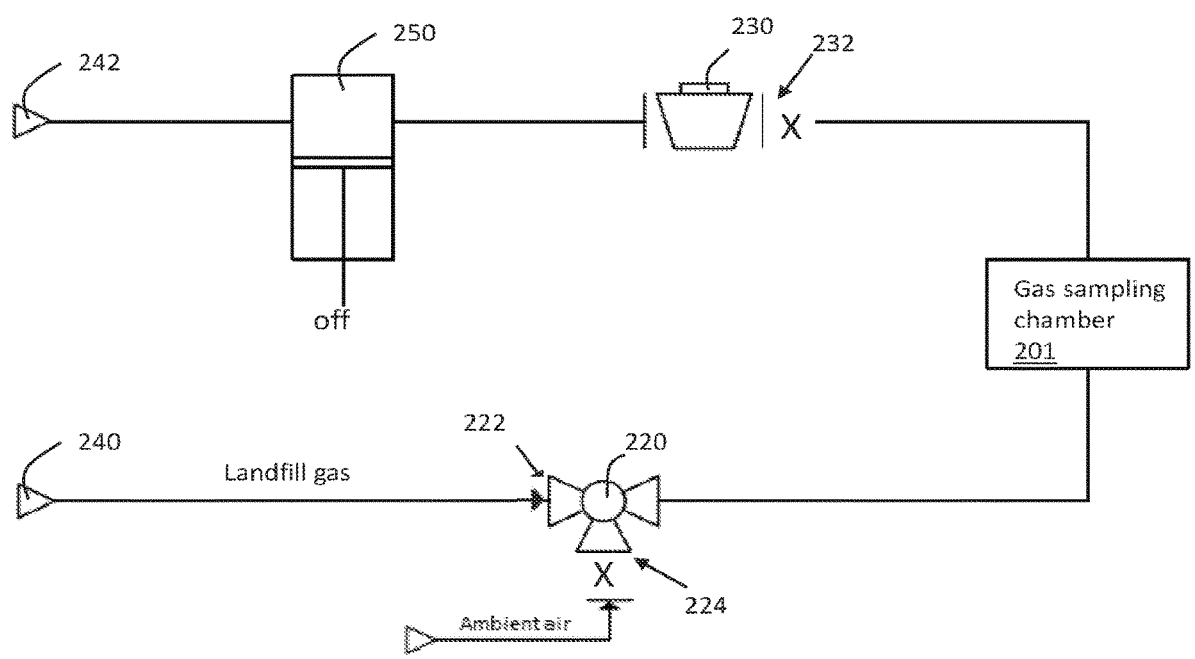
FIG. 3C is a process flow diagram illustrating exemplary components of the gas monitoring and control system of FIG. 3A implementing a vacuum measurement phase, according to at least one embodiment of the invention.

FIG. 3C is a process flow diagram illustrating exemplary components of the gas monitoring and control system of FIG. 3A implementing a vacuum measurement phase, according to at least one embodiment of the invention. In the vacuum measurement phase, the controller 210 causes the inlet sampling valve 220, the outlet sampling valve 230 and the gas sampling pump 250 to operate in a vacuum measurement state. In these embodiments, the controller 210 causes the landfill gas inlet port 222 of the inlet sampling valve 220 to open and causes the inlet port 232 of the outlet sampling valve 230 to close. Also, the controller 210 causes the gas sampling pump 250 to cease pumping (i.e., turn off). As a result, when there is a negative pressure presented inside the wellhead 10, a negative pressure in the gas sampling chamber 201 is also created, A static pressure sensor, connected to the gas sampling chamber 201 via a vacuum tube, measures vacuum pressure of the wellhead 10. The sensor output signals are subsequently transmitted to the controller 210 for further processing.

Figure 3D:
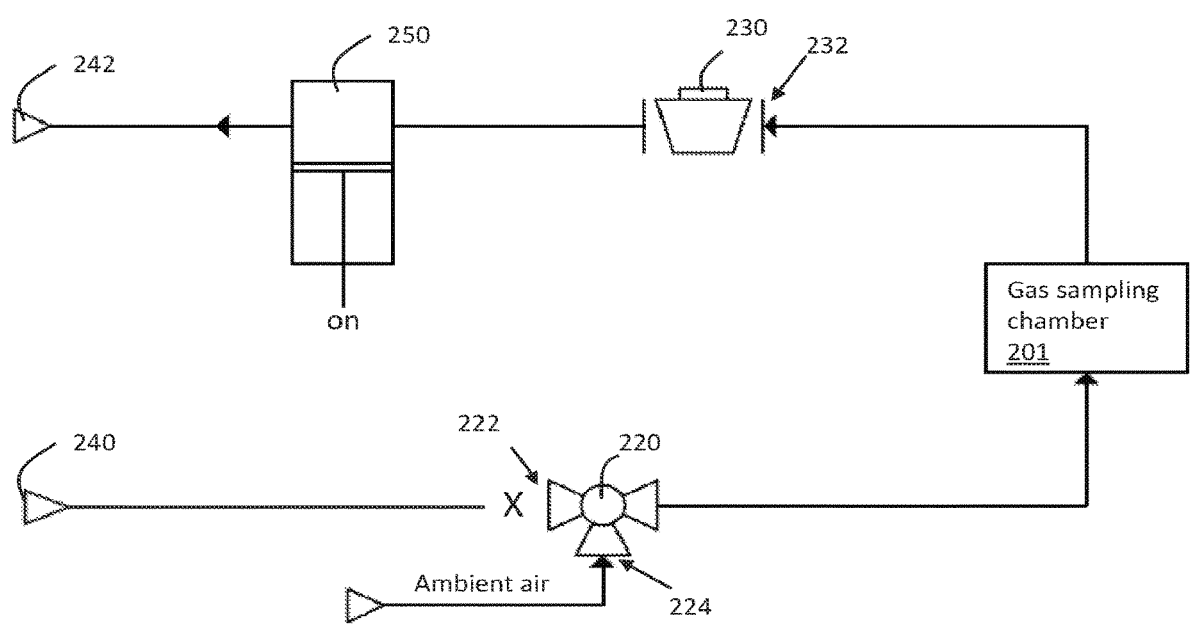
FIG. 3D is a process flow diagram illustrating exemplary components of the gas monitoring and control system of FIG. 3A implementing a purge phase, according to at least one embodiment of the invention.

FIG. 3D is a process flow diagram illustrating exemplary components of the gas monitoring and control system of FIG. 3A implementing a purge phase, according to at least one embodiment of the invention. In the purge phase, the controller 210 causes the inlet sampling valve 220, the outlet sampling valve 230 and the gas sampling pump 250 to operate in a purge state. In these embodiments, the controller 210 causes the ambient air inlet port 224 of the inlet sampling valve 220 to open and causes the inlet port 232 of the outlet sampling valve 230 to close. The controller 210 also causes the gas sampling pump 250 to pump ambient air through the gas sampling chamber 201. As a result, ambient air enters the gas sampling chamber 201, thereby purging the landfill gas from the gas sampling chamber 201.

Figure 3E:
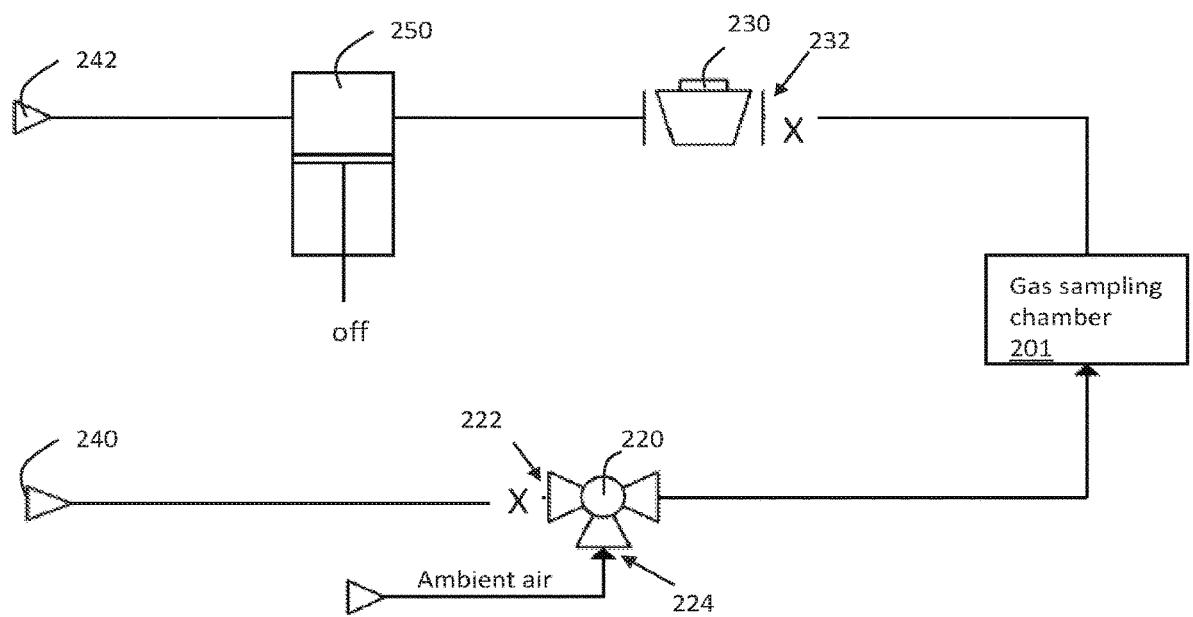
FIG. 3E is a process flow diagram illustrating exemplary components of the gas monitoring and control system of FIG. 3A implementing an isolation phase, according to at least one embodiment of the invention.

FIG. 3E is a process flow diagram illustrating exemplary components of the gas monitoring and control system of FIG. 3A implementing an isolation phase, according to at least one embodiment of the invention. In the isolation phase, the controller 210 causes the inlet sampling valve 220, the outlet sampling valve 230 and the gas sampling pump 250 to operate in an isolation state. In these embodiments, the controller 210 causes the ambient air inlet port 224 of the inlet sampling valve 220 to open and causes the inlet port 232 of the outlet sampling valve 230 to close. Also, the controller 210 causes the gas sampling pump 250 to cease pumping. As a result, the sensors in the gas sampling chamber 201 are isolated from the corrosive landfill gas to minimize the sensors exposure to the landfill gas and minimizing sensor degradation.

In some embodiments, the controller 210 receives one or more gas sampling commands to sample the landfill gas from an external computing device. In response, the controller 210 implements the gas sampling phase and/or vacuum measurement phase. Upon completion, the controller 210 implements the purge phase and the isolation phase. As a result, a technician can manually control sampling of the landfill gas at the wellhead 10 from an external computing device at a remote location.

In some embodiments, the sampling phase has a sampling time period of less than 10 seconds, less than 30 seconds, less than 1 minute, less than 5 minutes, less than 10 minutes, less than 30 minutes, less than 1 hour, less than 12 hours, or less than 24 hours.

In some embodiments, the purge phase has a purge time period of less than 10 seconds, less than 30 seconds, less than 1 minute, less than 5 minutes, less than 10 minutes, less than 30 minutes, less than 1 hour, less than 12 hours, or less than 24 hours.

In some embodiments, the isolation phase has an isolation time period of less than 10 seconds, less than 30 seconds, less than 1 minute, less than 5 minutes, less than 10 minutes, less than 30 minutes, less than 1 hour, less than 12 hours, or less than 24 hours.

In some embodiments, the vacuum measurement phase has a vacuum measurement time period of less than 10 seconds, less than 30 seconds, less than 1 minute, less than 5 minutes, less than 10 minutes, less than 30 minutes, less than 1 hour, less than 12 hours, or less than 24 hours.

In some embodiments, each of the gas sampling phase, the purge phase, the isolation phase and/or the vacuum measurement phase operate in non-overlapping time periods.

In some embodiments, the sampling time interval between successive sampling time periods is greater than 5 seconds, greater than 10 seconds, greater than 30 seconds, greater than 1 minute, greater than 5 minutes, greater than 10 minutes, greater than 30 minutes, greater than 1 hour, greater than 12 hours, greater than 24 hours, greater than 1 week, or greater than 1 month.

In some embodiments, the purge time interval between successive purge time periods is greater than 5 seconds, greater than 10 seconds, greater than 30 seconds, greater than 1 minute, greater than 5 minutes, greater than 10 minutes, greater than 30 minutes, greater than 1 hour, greater than 12 hours, greater than 24 hours, greater than 1 week, or greater than 1 month.

In some embodiments, the vacuum measurement time interval between successive vacuum measurement time periods is greater than 5 seconds, greater than 10 seconds, greater than 30 seconds, greater than 1 minute, greater than 5 minutes, greater than 10 minutes, greater than 30 minutes, greater than 1 hour, greater than 12 hours, greater than 24 hours, greater than 1 week, or greater than 1 month.

In some embodiments, the isolation time interval between successive isolation time periods is greater than 5 seconds, greater than 10 seconds, greater than 30 seconds, greater than 1 minute, greater than 5 minutes, greater than 10 minutes, greater than 30 minutes, greater than 1 hour, greater than 12 hours, greater than 24 hours, greater than 1 week, or greater than 1 month.

Valve Actuation

In certain situations, it may be favorable to regulate the amount of landfill gas expelled from the landfill area 11 based on the composition of landfill gas to optimize gas collection. For example, higher levels of methane in the landfill gas improves the recovery of energy through regeneration techniques, because higher levels of methane produce more energy when burned. In these situations, it may be favorable to increase the amount of landfill gas evacuating from the wellhead 10. In contrast, higher levels of oxygen in the landfill gas may indicate that the gas well is extracting more gas than is being produced by garbage decomposition. In these situations, it may be favorable to decrease the amount of landfill gas evacuating from the wellhead 10.

Figure 4:
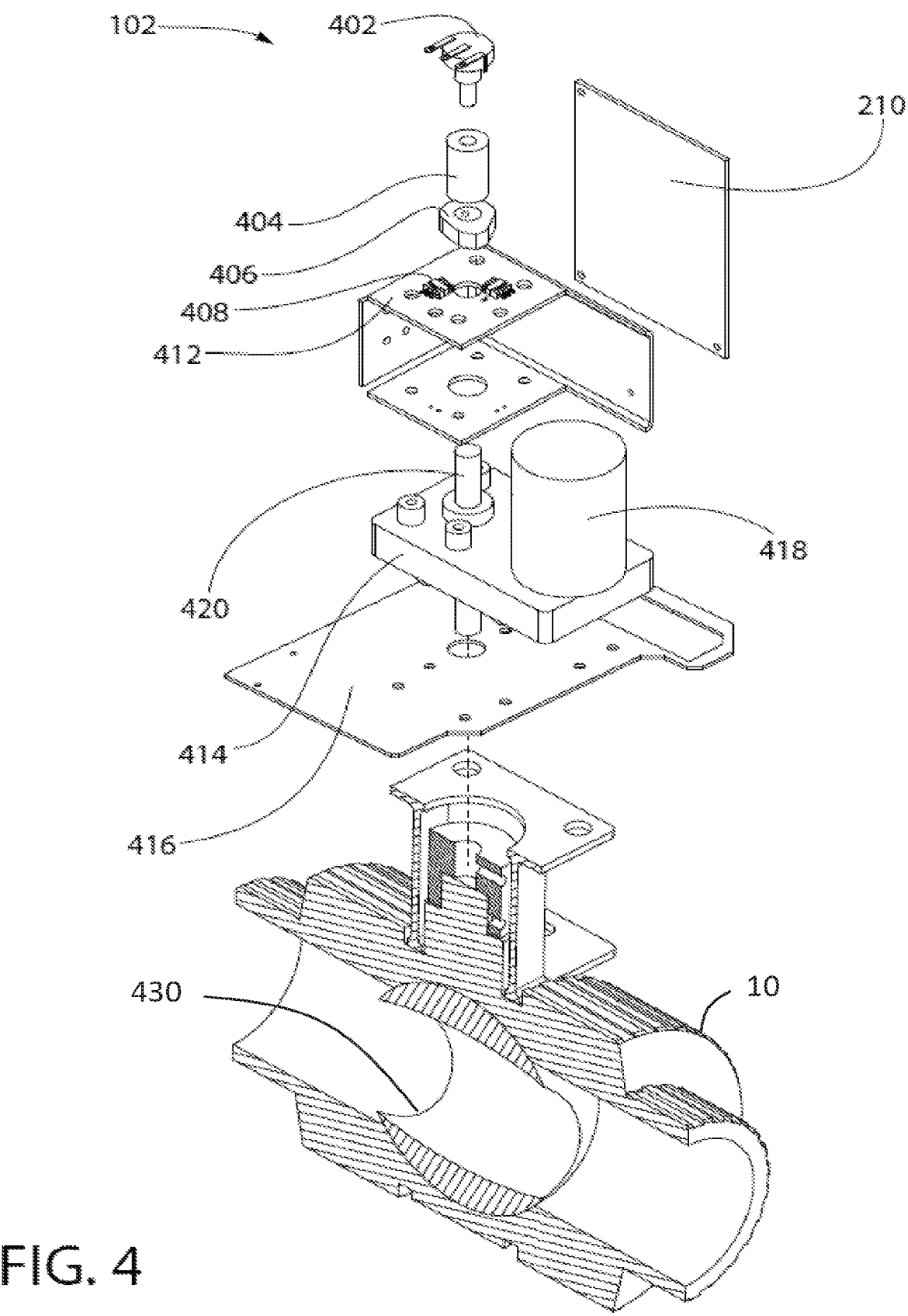
FIG. 4 shows an exploded perspective view of some of the exemplary components of the gas monitoring and control system for regulating landfill gas evacuation according to at least one embodiment of the invention.

FIG. 4 shows an exploded perspective view of some of the exemplary components of the gas monitoring and control system 102 for regulating landfill gas evacuation according to at least one embodiment of the invention. As shown, the gas monitoring and control system 102 includes a position sensor 402, a position sensor coupling 404, a limit trigger cam 406, a closed limit switch 408, an open limit switch 410, an actuator carriage 412, a gearbox 414, an enclosure mounting 416, a valve actuator motor 418, valve actuator shaft 420 and controller 210.

In some embodiments, the gas monitoring and control system 102 adjusts a position of a wellhead valve 430 in the wellhead 10 towards an open position or a closed position when sensor data collected by the sensors in the gas sampling chamber 201 to regulate landfill gas evacuation. For illustrative purposes, FIG. 4 shows a cutout of the wellhead valve 430 and the wellhead 10.

In some embodiments, the wellhead valve 430 is coupled to one end of the valve actuator shaft 420. The valve actuator motor 418 is also coupled to the valve actuator shaft 420 in a configuration that allows the valve actuator motor 418 to rotate the valve actuator shaft 420 using gearbox 414, In some embodiments, the valve actuator motor 418 causes valve actuator shaft 420 to rotate axially in response to receiving an electrical control signal from the controller 210. As the valve actuator shaft 420 rotates, the wellhead valve 430 rotates as well, causing a wellhead aperture to either increase or decrease in size.

In some embodiments, the controller 210 is configured to cause the wellhead valve 430 to rotate to an open position and a closed position. When the controller 210 causes the wellhead valve 430 to rotate toward an open position, an aperture size in the wellhead 10 increases, thereby increasing the amount of landfill gas evacuating to the main gas line 12. In the open position, the wellhead valve 430 substantially allows the landfill gas to evacuate through the wellhead 10. When the controller 210 causes the wellhead valve 430 to rotate toward a closed position, an aperture size in the wellhead 10 decreases, thereby decreasing the amount of landfill gas evacuating to the main gas line 12. In the closed position, the wellhead valve 430 substantially prevents the landfill gas from evacuating through the wellhead 10.

In some embodiments, a closed limit switch 408 and an open limit switch 410 are positioned on an actuator carriage 412 to prevent over-rotation of the wellhead valve 430. A limit trigger cam 406 is coupled to one end of the valve actuator shaft 420. As the valve actuator shaft 420 rotates, the limit trigger cam also rotates. When the valve actuator shaft 420 rotates to a closed position the limit trigger cam 406 contacts the closed limit switch 408. When the valve actuator shaft 420 rotates to an open position the limit trigger cam 406 contacts the open limit switch 410. When the limit trigger cam 406 contacts one of the limit switches 408, 410, the contacted limit switch transmits a contact alert to the controller 210. In response, the controller 210 ceases rotation of the wellhead valve 430.

In some embodiments, the controller 210 is configured to cause the wellhead valve 430 to rotate to one of a plurality of positions between the open position and the closed position. In these embodiments, a position sensor 402 (e.g., potentiometer) is positioned on an end of the wellhead valve shaft for valve position sensing. The position sensor 402 is coupled to the valve actuator shaft 420 via a position sensor coupling 404.

In some embodiments, controller 210 causes the wellhead valve 430 (e.g., via actuator shaft 420 and valve actuator motor 418) to rotate toward an open or closed position based on valve actuation criteria. Examples of valve actuation criteria may include i) one or more sensor signals exceeding or falling below a characteristic threshold for one or more characteristics (e.g., oxygen, methane, carbon dioxide) of the landfill gas; ii) a positive or negative rate of change of one or more sensor signals exceeding a change rate threshold; and iii) one or more sensor signals from a second wellhead separate from wellhead 10 being less than or greater than the one or more sensor signals from wellhead 10.

In some embodiments, an amount of a characteristic (e.g., oxygen) in the landfill gas is inversely proportional to the preferred amount of landfill gas evacuating from the wellhead 10. In these embodiments, if a sensor signal representative of an amount of a characteristic of the landfill gas exceeds a concentration threshold (e.g., 3% for oxygen), then controller 210 causes the wellhead valve 430 to rotate toward a closed position. In these embodiments, if a sensor signal representative of an amount of a characteristic of the landfill gas falls below a select threshold (e.g., 1% for oxygen), then controller 210 causes the wellhead valve 430 to rotate toward an open position. Conversely, if an amount of a characteristic (e.g., methane, carbon dioxide) in the landfill gas is proportional to the preferred amount of landfill gas evacuating from the wellhead 10, the controller 210 causes the wellhead valve 430 to rotate in the opposite direction.

In some embodiments, the rate of change of one or more characteristics (e.g., oxygen) of the landfill gas is inversely proportional to the preferred amount of landfill gas evacuating from the wellhead 10. In these embodiments, if a positive rate of change measured from multiple sensor signals over time exceeds a change rate threshold, then controller 210 causes the wellhead valve 430 to rotate towards a closed position. Also, in these embodiments, if a negative rate of change measured from multiple sensor signals over time falls below a change rate threshold, then controller 210 causes the wellhead valve 430 to rotate towards an open position. Conversely, if the rate of change of one or more characteristics of the landfill gas is proportional to the preferred amount of landfill gas evacuating from the wellhead 10, the controller 210 causes the wellhead valve 430 to rotate in the opposite direction.

By sampling the landfill gas at a substantially smaller time interval than a technician can inspect the wellhead 10, the gas monitoring and control system 102 can adjust the wellhead valve 430 more often, thereby allowing the landfill gas to evacuate from the wellhead 10 when the landfill gas has favorable characteristics.

In some embodiments, the wellhead 10 is one of a plurality of wellheads connected to the main gas line 12. In some situations, it may be beneficial to regulate landfill gas flow from the wellhead 10 based on landfill gas characteristics from another wellhead 10, For example, if a renewable energy facility can only receive a fixed amount of landfill gas over a certain time period (e.g., 1000 cu. ft./minute) and the wellhead 10 along with a second wellhead supply more landfill gas (e.g., 2000 cu. ft./minute) than the fixed amount, the excess landfill gas may be wasted for renewable energy purposes, To address this problem, in some embodiments, controller 210 may be configured to receive data (e.g., sensor data or commands from a remote computing device) representative of landfill gas at a second wellhead and cause the wellhead valve 430 to rotate towards either an open position or closed position based on the sensor data representative of landfill gas at the wellhead 10 as well as sensor data representative of landfill gas at the second wellhead separate from the wellhead 10. For example, if the gas characteristics of the landfill gas from the second wellhead is more favorable than the gas characteristics of the landfill gas from the wellhead 10 (e.g., has a higher level of methane concentration than the landfill gas in the wellhead 10), controller 210 may cause the wellhead valve 430 to rotate towards a closed position while a controller at the second wellhead may cause the wellhead valve of the second wellhead to rotate towards an open position, or vice versa. Alternatively, if the gas characteristics of the landfill gas from the wellhead 10 is more favorable than the gas characteristics of the landfill gas from the second wellhead (e.g., has a higher level of methane concentration than the landfill gas in the second wellhead), controller 210 may cause the wellhead valve 430 to rotate towards an open position while a controller at the second wellhead may cause the wellhead valve of the second wellhead to rotate towards a closed position, or vice versa. As a result, the renewable energy facility receives landfill gas having a more favorable composition as a combination of the landfill gas from the wellhead 10 and the landfill gas from the second wellhead.

In some embodiments, the plurality of wellheads is greater than greater2; than 3; greater than 4; greater than 5; greater than 10; greater than 20; greater than 50; greater than 100; greater than 200; or greater than 500. As the number of wellheads increases, continuous and automatic monitoring using technicians that physically visit each wellhead becomes technically challenging and cost-prohibitive. As a result, a single technician or computing device can monitor landfill gas from a plurality of wellheads and adjust the respective wellhead valves of the wellheads in real-time to optimize the landfill gas composition in the main gas line 12.

Safety/Diagnostic

In some embodiments, the controller 210 is configured to detect dangerous or undesirable operating conditions within the housing 101. Examples of dangerous or undesirable operating conditions include, but are not limited to: component failures, high ambient methane levels, and required maintenance detection. In response to detecting a dangerous or undesirable operating condition, the controller 210 transmits an alert to a user at a remote computing device.

In some embodiments, a methane sensor is positioned within the housing 101 but outside of the gas sampling chamber 201 to measure ambient methane levels. The sensor data of the methane sensor is transmitted to the controller

210. The controller 210 is configured to determine whether levels of ambient methane meet ambient methane safety criteria (e.g., exceeds a select ambient methane threshold). When the level of ambient methane meets the ambient methane safety criteria, controller 210 may cease actuation of the wellhead valve 430, and/or generate and transmit an alert to a user at a remote computing device.

In some embodiments, the controller 210 includes current feedback sensing of the valve actuator motor 418, sampling valves 420, 430 and/or gas sampling pump 250. Current feedback sensing of the motor 418, sampling valves 420, 430 and pump 250 can be used to detect solenoid valve failures, condensate build up within the pump or gas sampling lines, or pump or motor failure, among others. When the current feedback sensing meets the current feedback safety criteria (e.g., exceeds a select current feedback threshold), controller 210 may cease actuation of the actuator motor 418, sampling valves 420, 430 and/or gas sampling pump 250, and/or generate and transmit an alert to a user at a remote computing device.

In some embodiments, the controller 210 is configured to generate and transmit an alert if a sensor signal (e.g., from sensors 204, 206, 208) meets sensor signal alert criteria (e.g., exceeds a select threshold). For example, in some embodiments, the controller 210 may generate an alert if the oxygen concentration, measured by the oxygen sensor 204 exceeds 5% of the total composition of the landfill gas. In some embodiments, the controller 210 may generate an alert if the methane or carbon dioxide concentration, measured by the methane/carbon dioxide sensor 206 exceeds 50% of the total composition of the landfill gas. In some embodiments, the controller 210 may generate an alert if the humidity, measured by the humidity sensor 208 exceeds 90% relative humidity. When a sensor signal meets sensor signal alert criteria, it may indicate that there is a problem with the wellhead 10 requiring physical inspection by a technician.

General Computer/Communications

Figure 5:
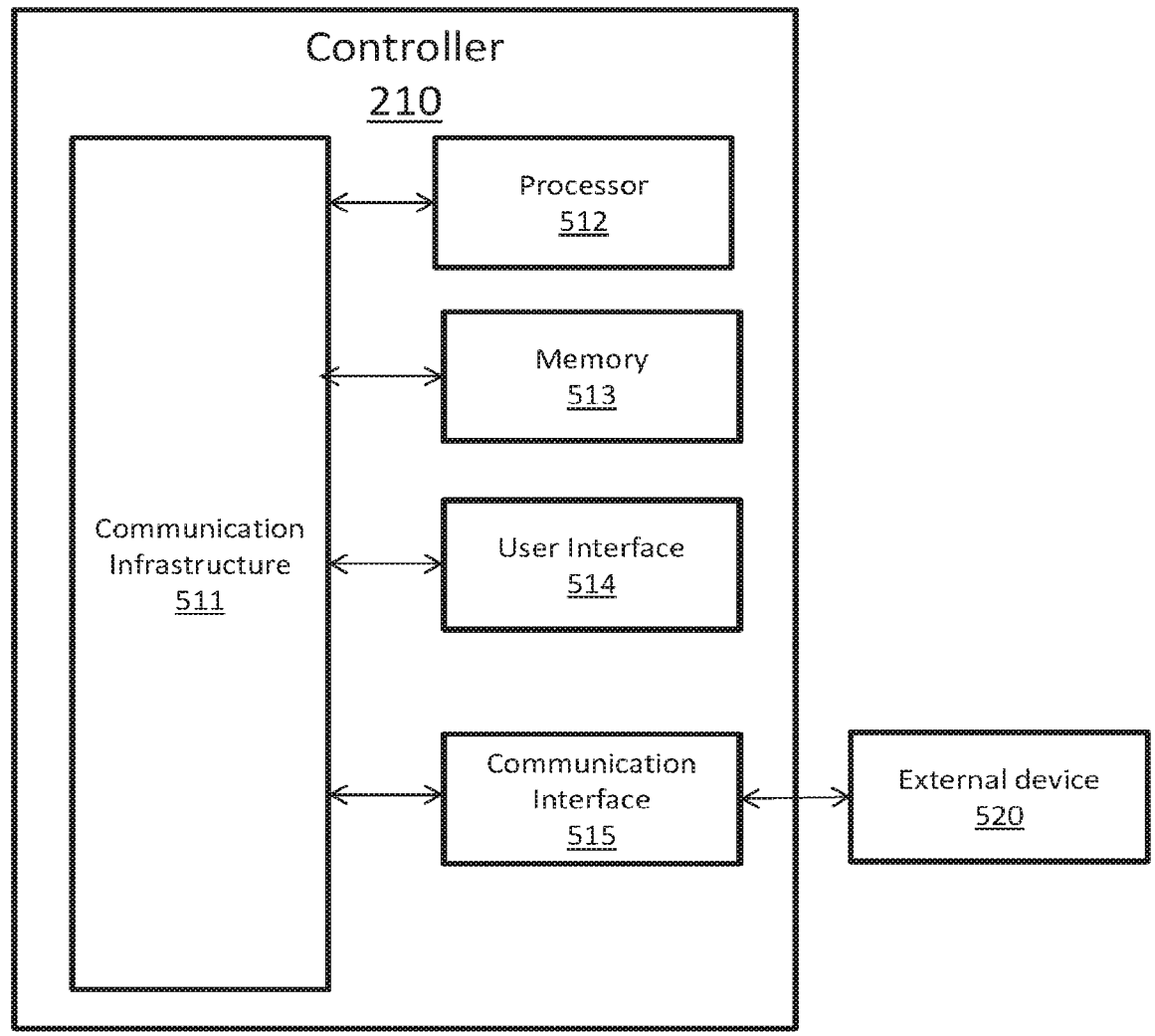
FIG. 5 is a diagram of the controller shown in FIG. 2, according to at least one embodiment of the invention.

FIG. 5 is a diagram of controller 210 shown in FIG. 2, according to at least one embodiment of the invention.

Controller 210 includes a processor 512. Processor 512 may be any type of processor, including but not limited to a special purpose or a general-purpose digital signal processor. Processor 512 may be connected to a communication infrastructure 511 (e.g. a data bus or computer network) either via a wired connection or a wireless connection. Communication infrastructure 511 carries signals and may be implemented using wire or cable, fiber optics, a phone line, a wireless link, a cellular phone link, a radio frequency link, or any other suitable communication channel, including a combination of the foregoing exemplary channels.

Controller 210 includes memory 513. Memory 513 may include at least one of random access memory (RAM), a hard disk drive and a removable storage drive, such as a floppy disk drive, a magnetic tape drive, or an optical disk drive. The removable storage drive reads from and/or writes to a removable storage unit. The removable storage unit can be a floppy disk, a magnetic tape, an optical disk, which is read by and written to a removable storage drive.

In alternative implementations, memory 513 may include other similar means for allowing computer programs or other instructions to be loaded into controller 210. Examples may include a removable storage unit and an interface. Examples may include a removable memory chip (such as an EPROM, or PROM, or flash memory) and associated socket, and other removable storage units and interfaces which allow data to be transferred from removable storage unit to controller 210. Alternatively, the program may be executed and/or the data accessed from the removable storage unit, using the processor 512 of the controller 210.

Controller 210 includes a user interface 514. User interface 514 may be a program that controls a display (not shown) of controller 210, on which the output of the processes described herein can be displayed. User interface 514 may include one or more peripheral user interface components, such as a keyboard or a mouse. The end user may use the peripheral user interface components to interact with controller 210. User interface 514 may receive user inputs, such as mouse inputs or keyboard inputs from the mouse or keyboard user interface components.

Controller 210 may, also include a communication interface 515. Communication interface 515 allows data to be transferred between controller 210 and an external device 520 (e.g., central control system). Examples of communication interface 515 may include a modem, a network interface (such as an Ethernet card), and a communication port, by way of example. Data transferred via communication interface 515 are in the form of signals, which may be electronic, electromagnetic, optical, or other signals capable of being received by communication interface 515. These signals are provided to communication interface 515 via a communication infrastructure 511.

In some embodiments, the external device 520 may be outside of a transmission range of the communication interface 515. In these embodiments, if a second gas monitoring and control system positioned at another wellhead is inside the transmission range of the communication interface 515, the communication interface 515 may communicate with the external device via the second gas monitoring and control system via a mesh network using Digimesh or ZigBee protocols.

In some embodiments, the controller 210 receives power from a fixed power source (e.g., a battery). In some embodiments, the controller 210 receives power from a regenerative power source (e.g., solar panels). In some embodiments, one or more solar panels are positioned on the housing 101 to provide direct power to the controller 210 or recharge the fixed power source.

Figure 6:
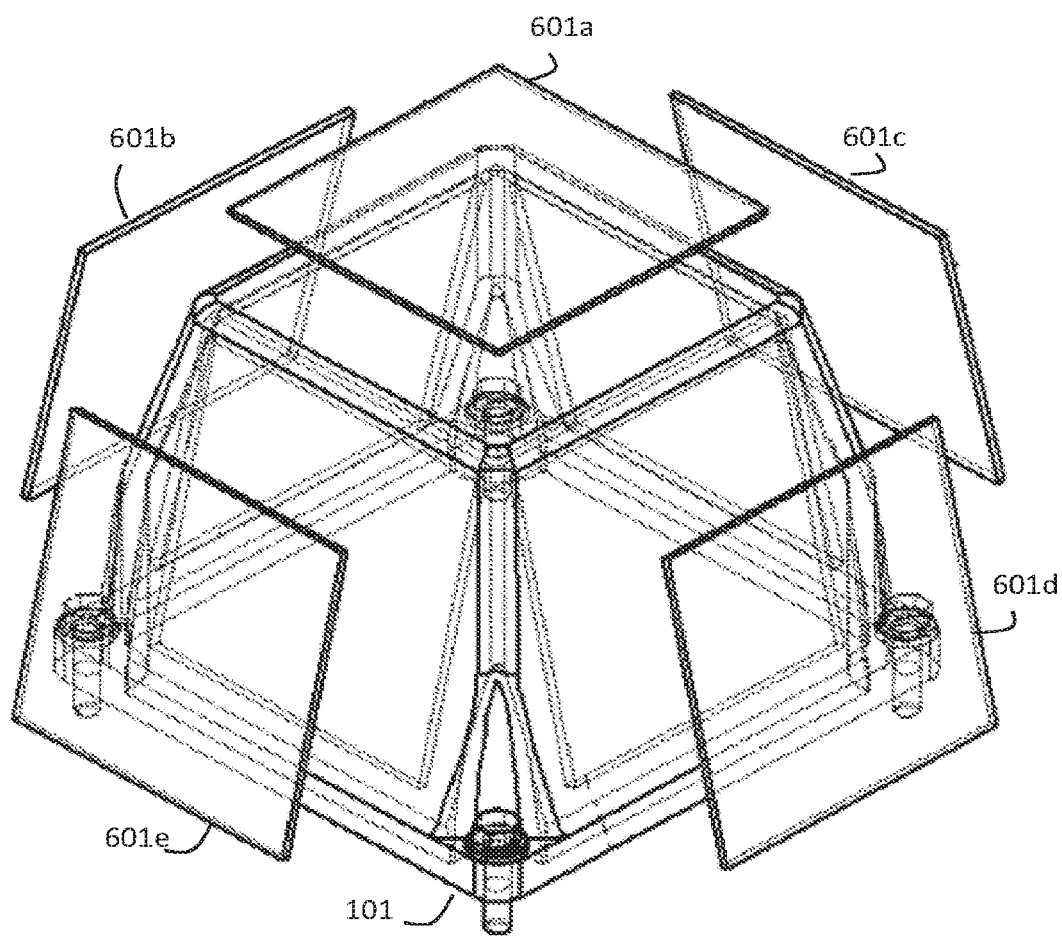
FIG. 6 shows a perspective view of the housing of system according to at least one embodiment of the invention.

FIG. 6 shows a perspective view of the housing 101 of the system 100 according to at least one embodiment of the invention. In FIG. 6, a plurality of solar panels 601*a*, 601*b*, 601*c*, 601*d*, 601*e*, may be positioned on the housing 101. In some embodiments, the plurality of solar panels may be positioned omni-directionally to maximize exposure to the sun and thereby maximize power generation via solar power.

Alternative Embodiments

It is contemplated that embodiments of the invention described herein for landfill gas extraction are exemplary, and that embodiments of the invention extend beyond use solely in the landfill gas extraction field to any technology or system that involves detection of flow, emission or composition of gas or liquid. This includes early detection and mitigation of gas transport pipes leaks, both in municipal and industrial settings. Embodiments of the invention can facilitate large natural gas pipeline leak detection, or within a landfill's internal gas transport system. Embodiments of the invention may be used for urban planning by monitoring old or damaged gas lines throughout cities and detecting aberrational migratory gases. Embodiments of the invention can also be used for natural gas drill sites such as those in the Marcellus Shale to detect migratory gases, control flow valves, or use lower Explosive or flammable Limit sensors to warn workers of an unsafe environment.

Embodiments of the invention may be used in agricultural applications. In these embodiments, sensors, such as soil moisture sensors, may assess crop health and respond to such feedback, by, for example, controlling a water flow valve for irrigation. Thus, the foregoing examples and description of the embodiments of the invention described herein should be interpreted as illustrating, rather than as limiting, the present invention as defined herein. All variations and combinations of the features above are intended to be within the scope of this application and the following claims.

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A gas monitoring and control system comprising:
a gas sampling chamber having a chamber inlet, a chamber outlet and an interior chamber;
one or more sensors disposed within the interior chamber, the sensors being operable to sense one or more characteristics of a gas from a gas source and generate one or more sensor signals representative of the one or more characteristics of the gas;
a sampling inlet valve in operable communication with an outlet of the gas source and the chamber inlet;
a sampling outlet valve in operable communication with the chamber outlet and an inlet of the gas source, the sampling inlet valve and the sampling outlet valve operable to i) allow the gas from the gas source to enter the gas sampling chamber, and ii) allow ambient air to enter the gas sampling chamber,
a pump in operable communication with the sampling inlet valve and the sampling outlet valve, the pump operable to i) cause the gas to flow through the gas sampling chamber and ii) cause ambient air to flow through the gas sampling chamber; and
a controller in operable communication with the one or more sensors, the sampling inlet valve, the sampling outlet valve and the pump, the controller operable to cause the sampling inlet valve, the sampling outlet valve and the pump to operate in different states to selectively expose the one or more sensors to the gas.

2. The gas monitoring and control system of claim 1, wherein the sampling inlet valve and the sampling outlet valve are operable to facilitate creating a static pressure in the gas sampling chamber; and wherein the controller is operable to cause the sampling inlet valve and the sampling outlet valve to each operate in different states.

3. The gas monitoring and control system of claim 1, wherein the sampling inlet valve and the sampling outlet valve are operable to isolate the gas sampling chamber from the gas; and wherein the controller is operable to cause the sampling inlet valve and the sampling outlet valve to operate in different states.

4. The gas monitoring and control system of claim 1, wherein the controller is operable to cause the sampling inlet valve, the sampling outlet valve and the pump to operate in response to receiving a sampling command from an external computing device to sample the gas.

5. The gas monitoring and control system of claim 1, further comprising a valve actuator in operable communication with a gas source valve in the gas source; and wherein the controller is in operable communication with the valve actuator and operable to cause the valve actuator to transition the gas source valve towards an open position or a closed position when the one or more sensor signals meets valve actuation criteria to regulate the flow of the gas in the gas source.

6. The gas monitoring and control system of claim 5, wherein the one or more sensor signals includes a sensor signal representative of oxygen concentration of the gas.

7. The gas monitoring and control system of claim 5, wherein the one or more sensor signals meets valve actuation criteria when the one or more sensor signals exceeds a concentration threshold; and wherein the controller causes the valve actuator to transition the gas source valve towards the closed position when the one or more sensor signals exceeds the concentration threshold.

8. The gas monitoring and control system of claim 5, wherein the one or more sensor signals meets valve actuation criteria when the one or more sensor signals falls below a concentration threshold; and wherein the controller causes the valve actuator to transition the gas source valve towards the open position when the one or more sensor signals falls below the concentration threshold.

9. The gas monitoring and control system of claim 5 wherein the one or more sensor signals meets valve actuation criteria when a positive rate of change of the one or more sensor signals exceeds a concentration change rate threshold; and wherein the controller causes the valve actuator to transition the gas source valve towards the closed position when the positive rate of change of the one or more sensor signals exceeds the concentration change rate threshold.

10. The gas monitoring and control system of claim 5 wherein the one or more sensor signals meets valve actuation criteria when a negative rate of change of the one or more sensor signals exceeds a concentration change rate threshold; and wherein the controller causes the valve actuator to transition the gas source valve towards the open position when the negative rate of change of the one or more sensor signals exceeds the concentration change rate threshold.

11. The gas monitoring and control system of claim 5, wherein the controller is operable to cause the valve actuator to transition the gas source valve towards the open position or the closed position when a second set of one or more sensor signals sampled at a second gas source meets a second valve actuation criteria.

12. The gas monitoring and control system of claim 11, wherein the second set of one or more sensor signals meets the second valve actuation criteria when the second set of one or more sensor signals is less than the one or more sensor signals; and wherein the controller is operable to cause the valve actuator to transition the gas source valve towards the open position when the second set of one or more sensor signals is less than the one or more sensor signals.

13. The gas monitoring and control system of claim 11, wherein the second set of one or more sensor signals meets the second valve actuation criteria when the second set of one or more sensor signals is greater than the one or more sensor signals; and wherein the controller is operable to cause the valve actuator to transition the gas source valve towards the closed position when the second set of one or more sensor signals is greater than the one or more sensor signals.

\* \* \* \* \*